United States Patent
Kriesel et al.

[11] Patent Number: 6,010,482
[45] Date of Patent: Jan. 4, 2000

[54] APPARATUS FOR INDICATING FLUID PRESSURE IN A CONDUIT

[75] Inventors: Marshall S. Kriesel, St. Paul; Steven M. Arnold, Minnetonka; James Garrison, Minneapolis; Farhad Kazemzadeh, Bloomington, all of Minn.

[73] Assignee: Science Incorporated, Bloomington, Minn.

[21] Appl. No.: 08/906,382

[22] Filed: Aug. 5, 1997

Related U.S. Application Data

[60] Division of application No. 08/718,686, Sep. 24, 1996, Pat. No. 5,721,382, which is a continuation-in-part of application No. 08/432,220, May 1, 1995, abandoned.

[51] Int. Cl.[7] .................................................. A61M 37/00
[52] U.S. Cl. ........................ 604/131; 604/246; 604/890.1
[58] Field of Search ............... 604/132, 30, 48, 604/65, 66, 67, 246, 131, 260; 73/861.47, 706

[56] References Cited

U.S. PATENT DOCUMENTS

| | | | |
|---|---|---|---|
| 4,431,425 | 2/1984 | Thompson et al. | 604/246 |
| 4,626,243 | 12/1986 | Singh et al. | 604/141 |
| 5,039,279 | 8/1991 | Netwick et al. | 417/63 |
| 5,267,900 | 12/1993 | Dirr, Jr. et al. | 604/253 |

*Primary Examiner*—Corrine McDermott
*Assistant Examiner*—Kent Gring
*Attorney, Agent, or Firm*—James E. Brunton

[57] ABSTRACT

An apparatus for visually indicating fluid flow through a fluid system or apparatus such as a medical infusion device. The apparatus comprises a pair of thin, indicia bearing films disposed in an overlaying relationship. These films are shifted relative to each other by movement of mechanical actuators which are deflected solely by the pressure of the fluid within the fluid conduits of the system of the apparatus. The two films are stacked in closed proximity and are preferably constructed from a substantially transparent flexible material such as mylar. One surface of the inferior film is printed with a plurality of integrated symbols depicting various fluid flow conditions. The superior film functions as a mask over the inferior film and is printed with a pattern of diagonally extending, alternating clear and opaque stripes. The print ratio of the superior film permits viewing at any one time of only one of the symbols printed on the inferior film.

34 Claims, 14 Drawing Sheets

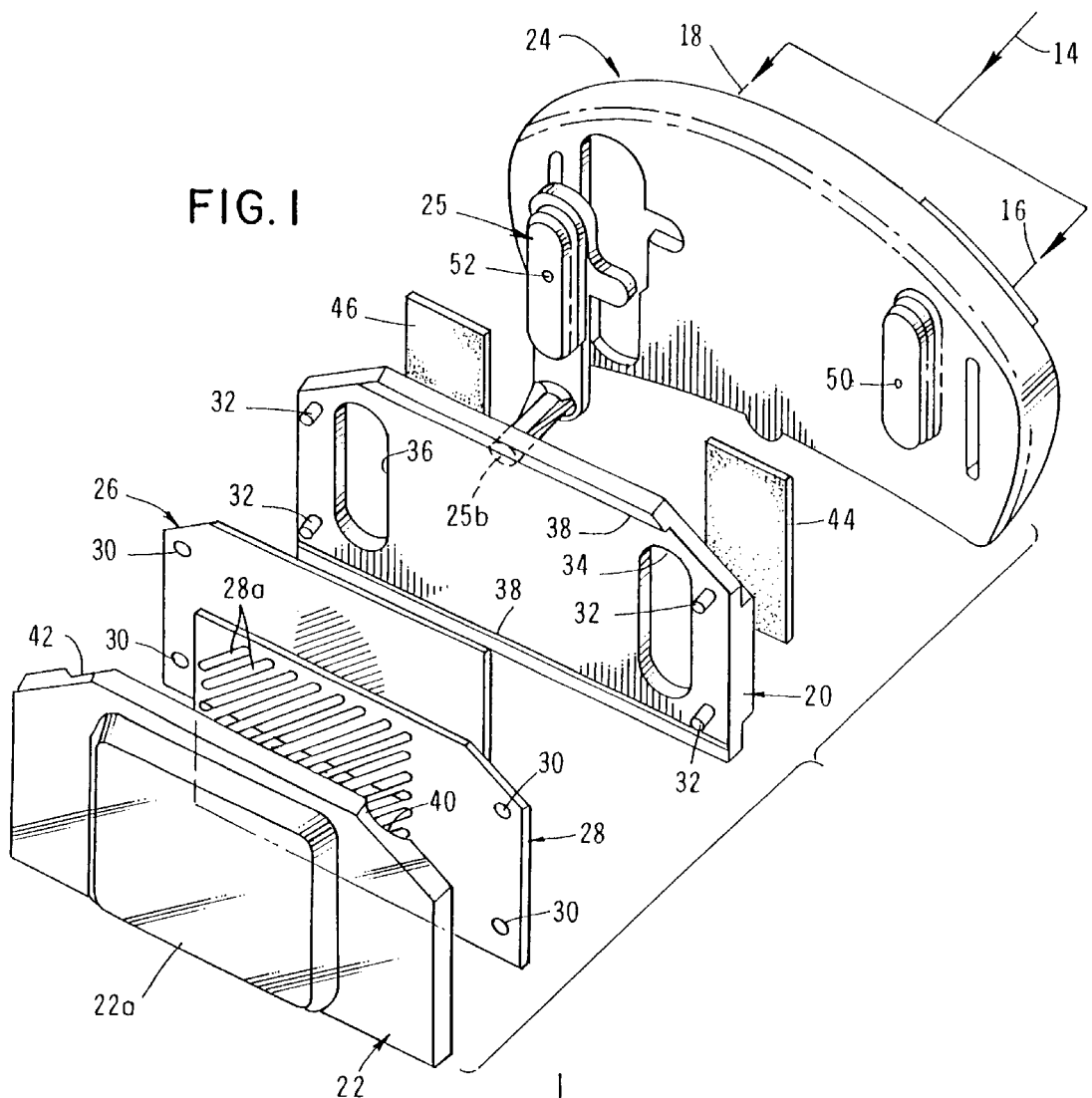

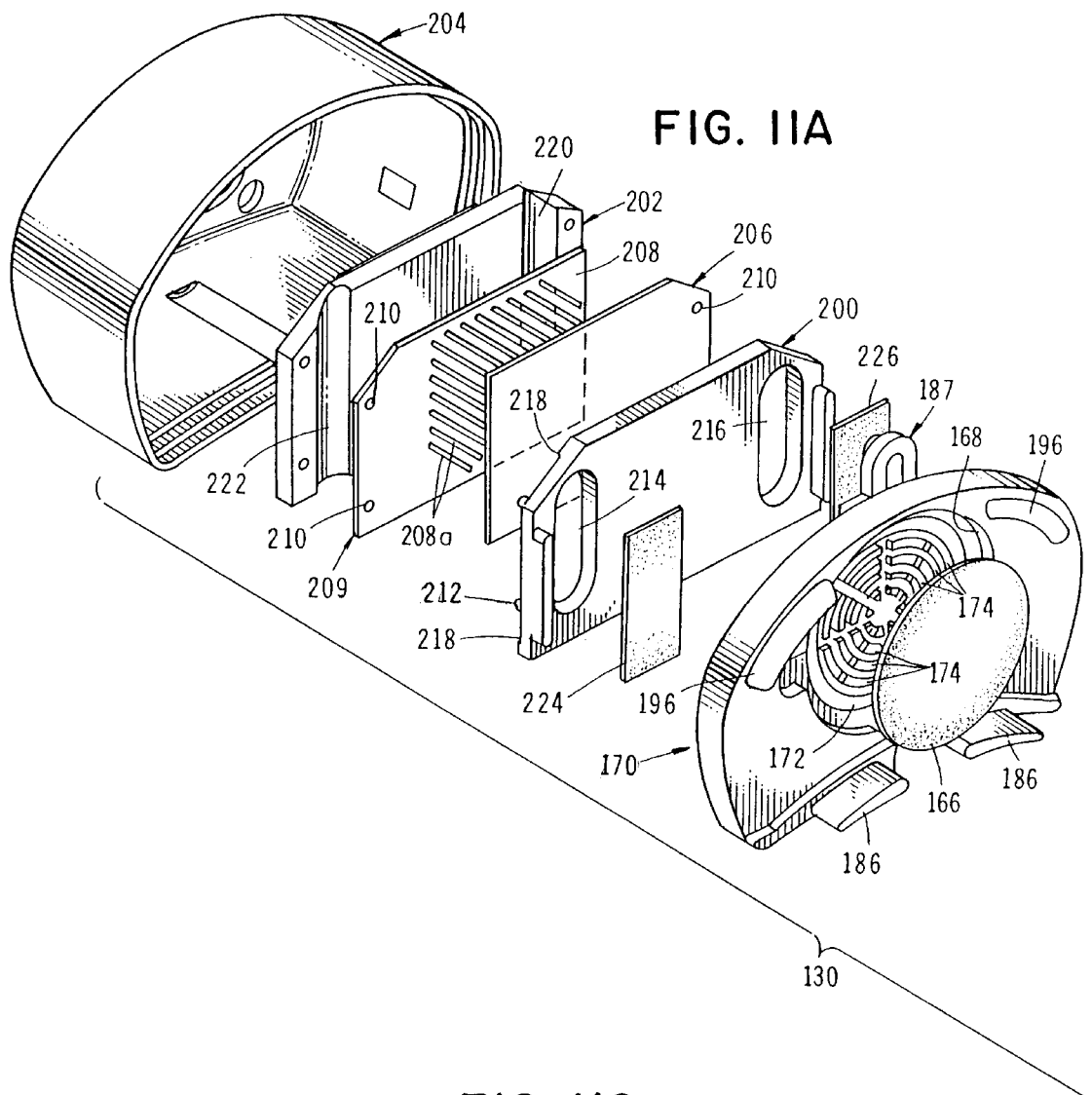
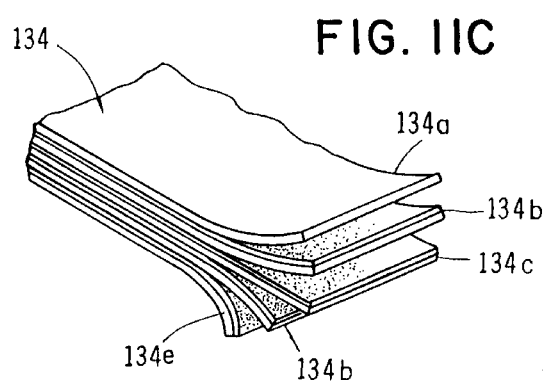

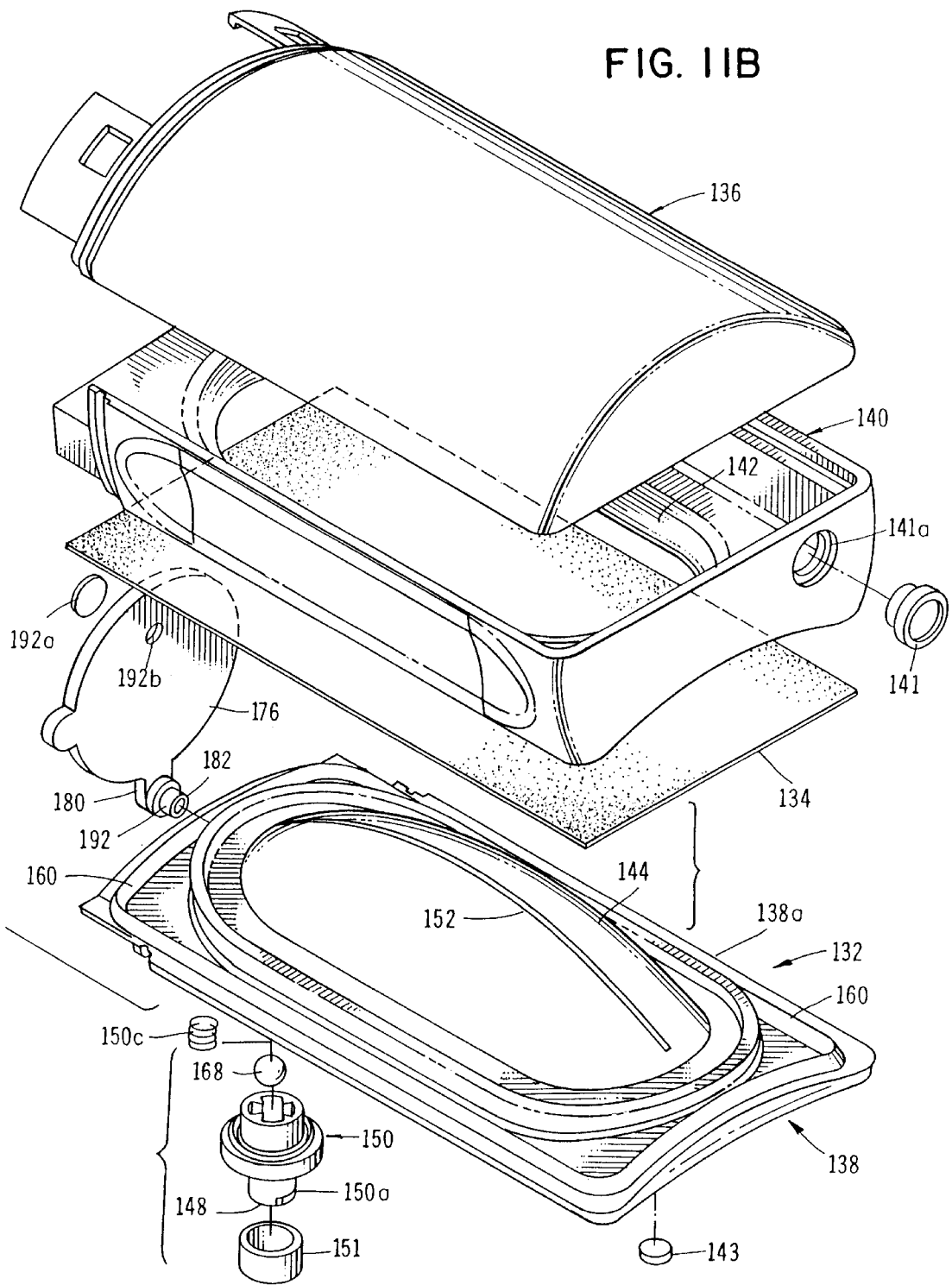

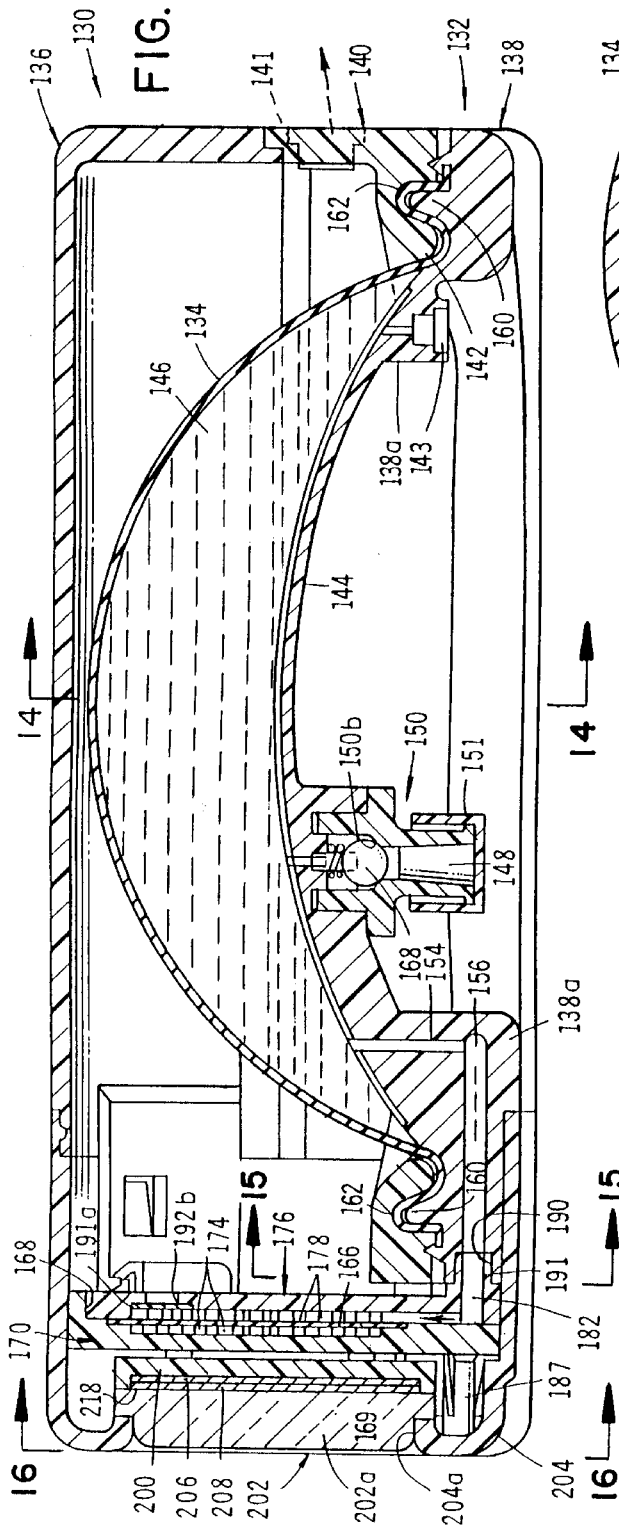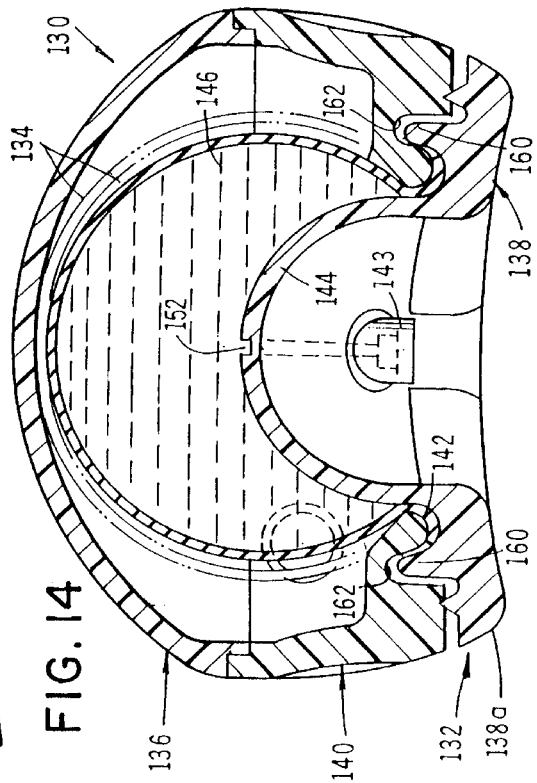

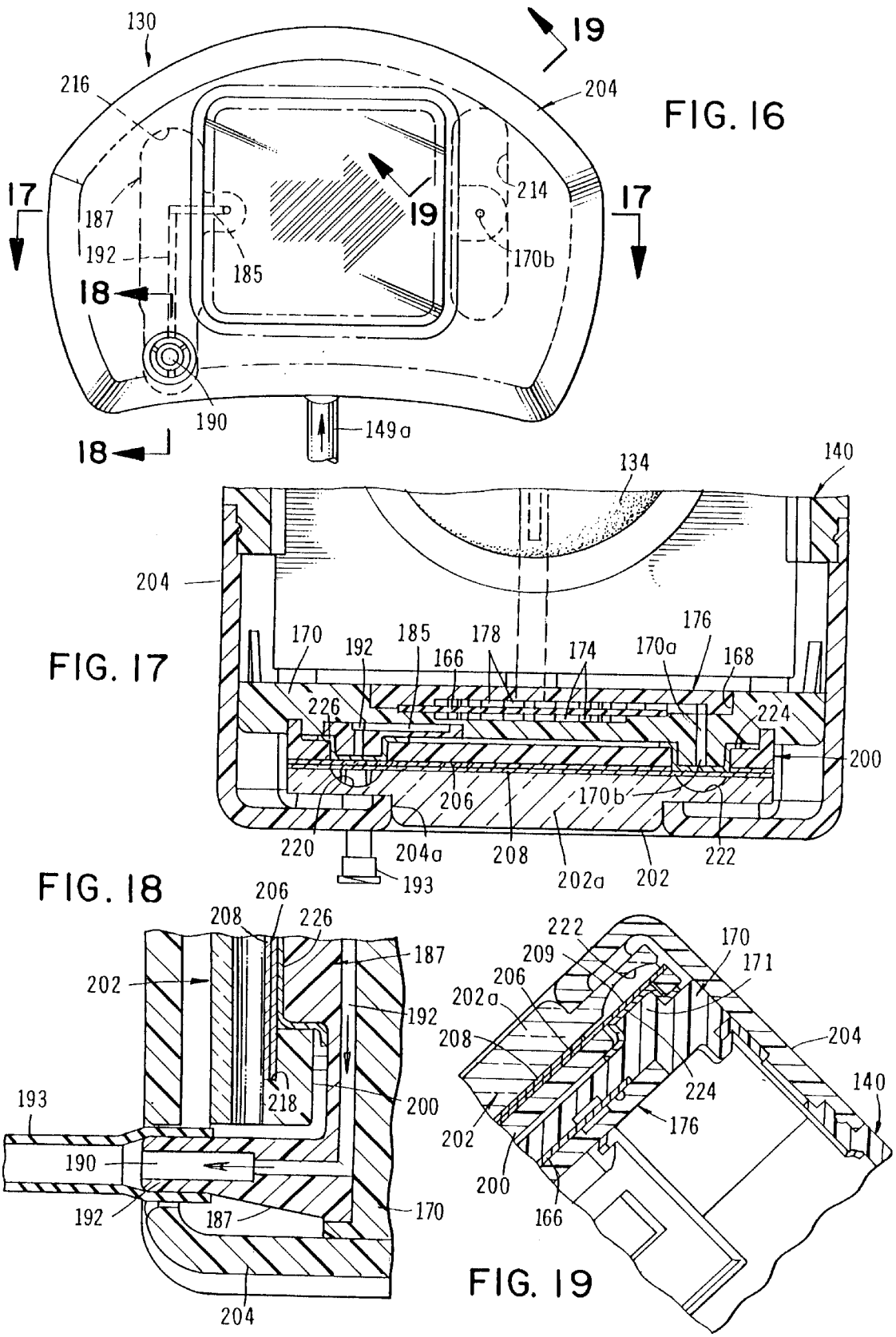

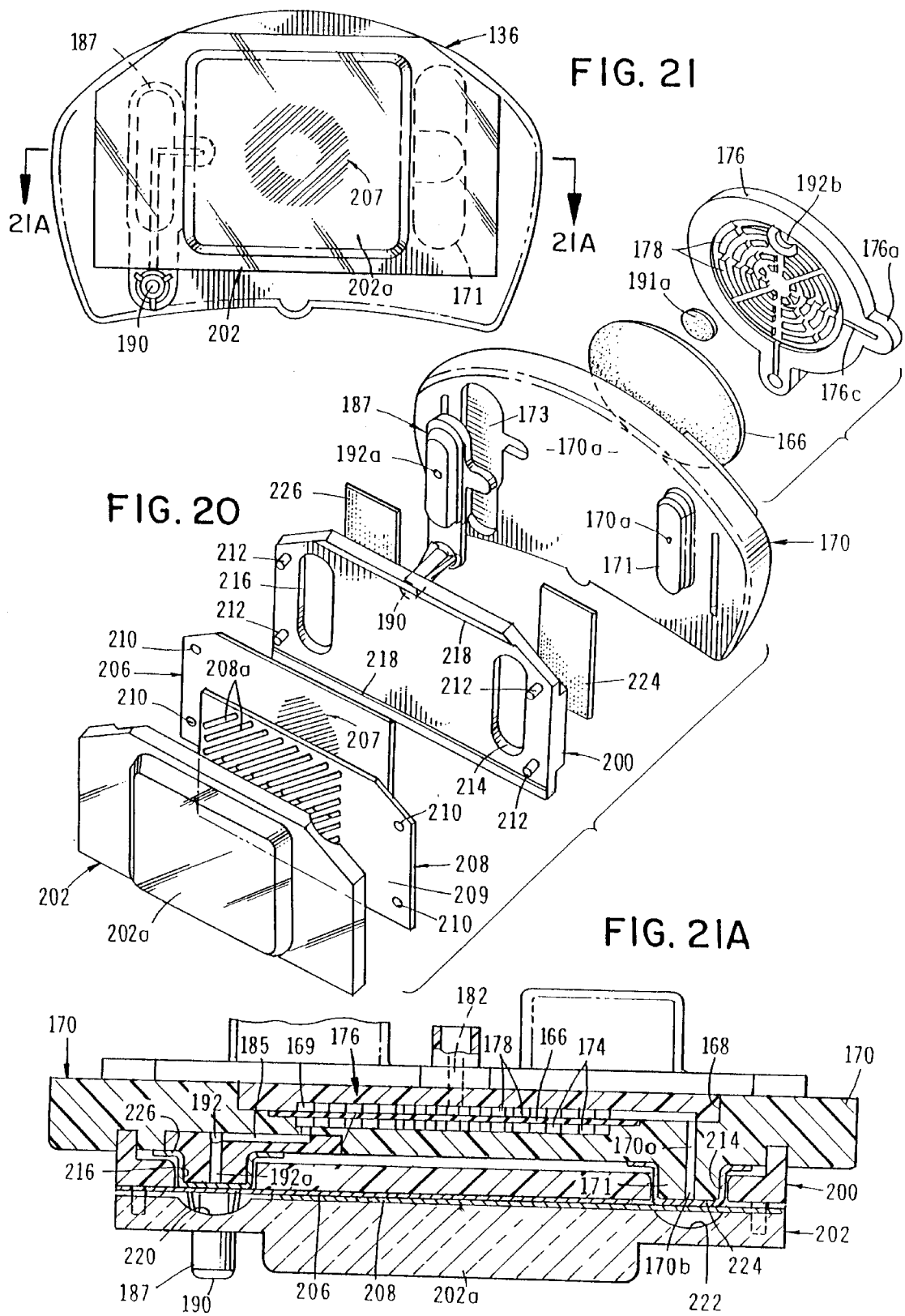

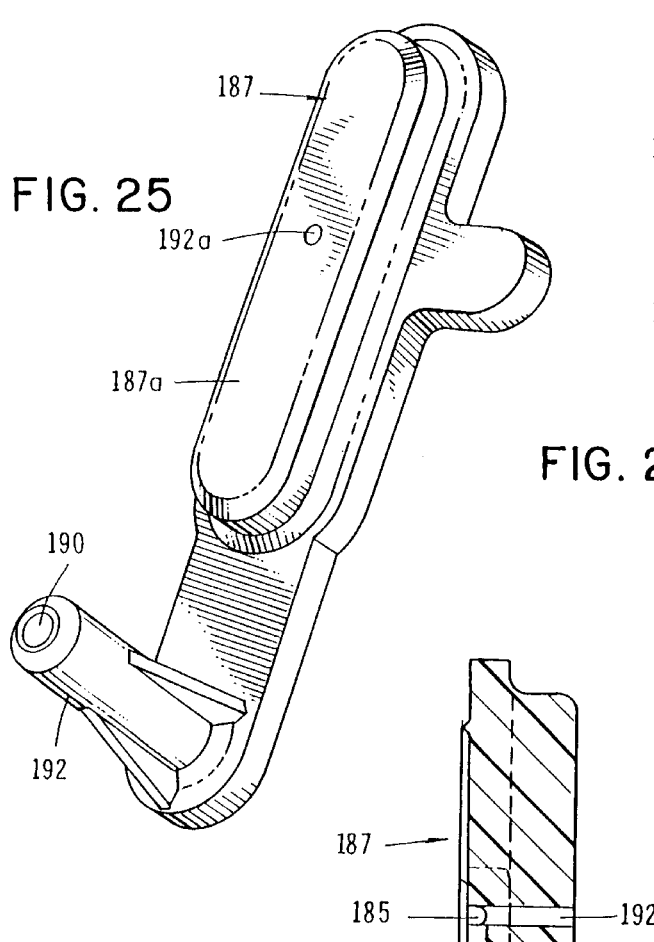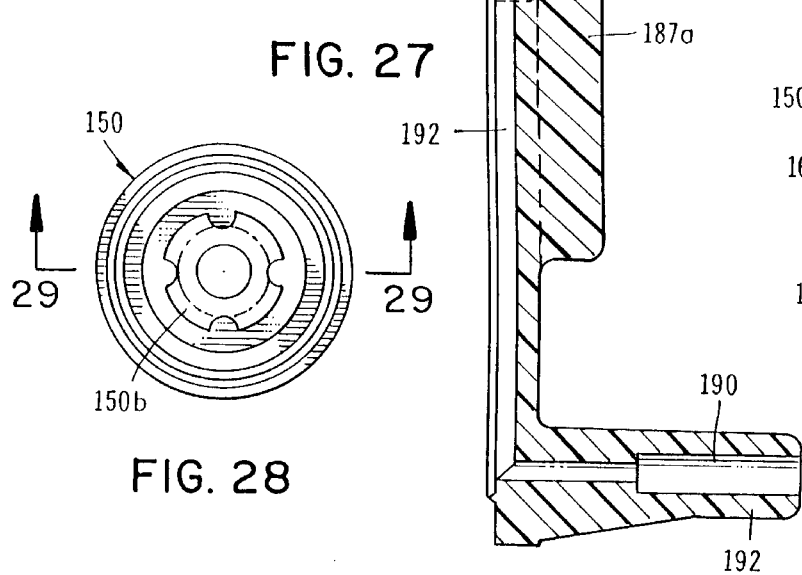

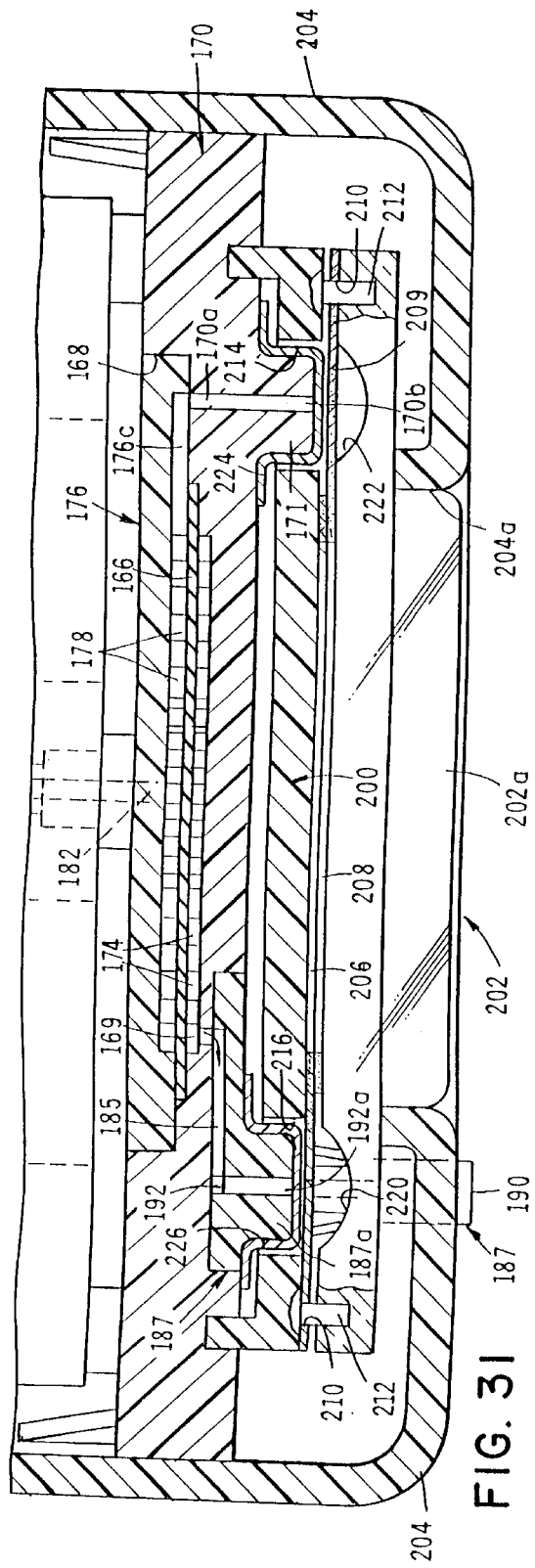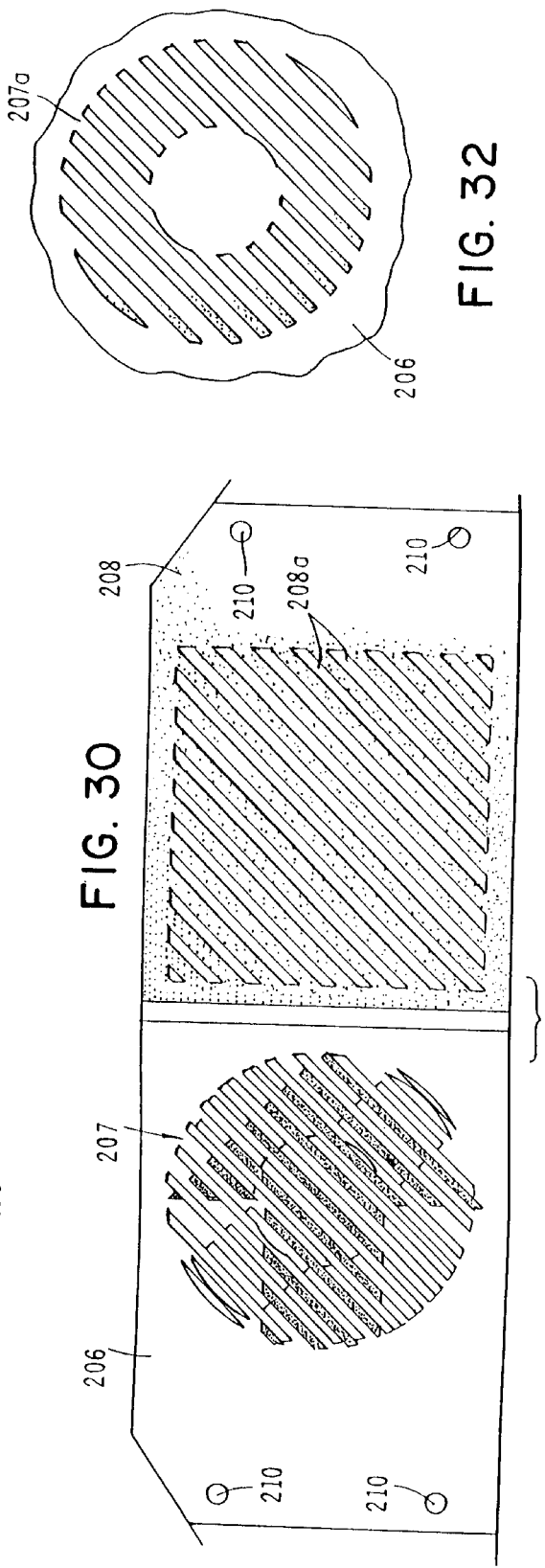

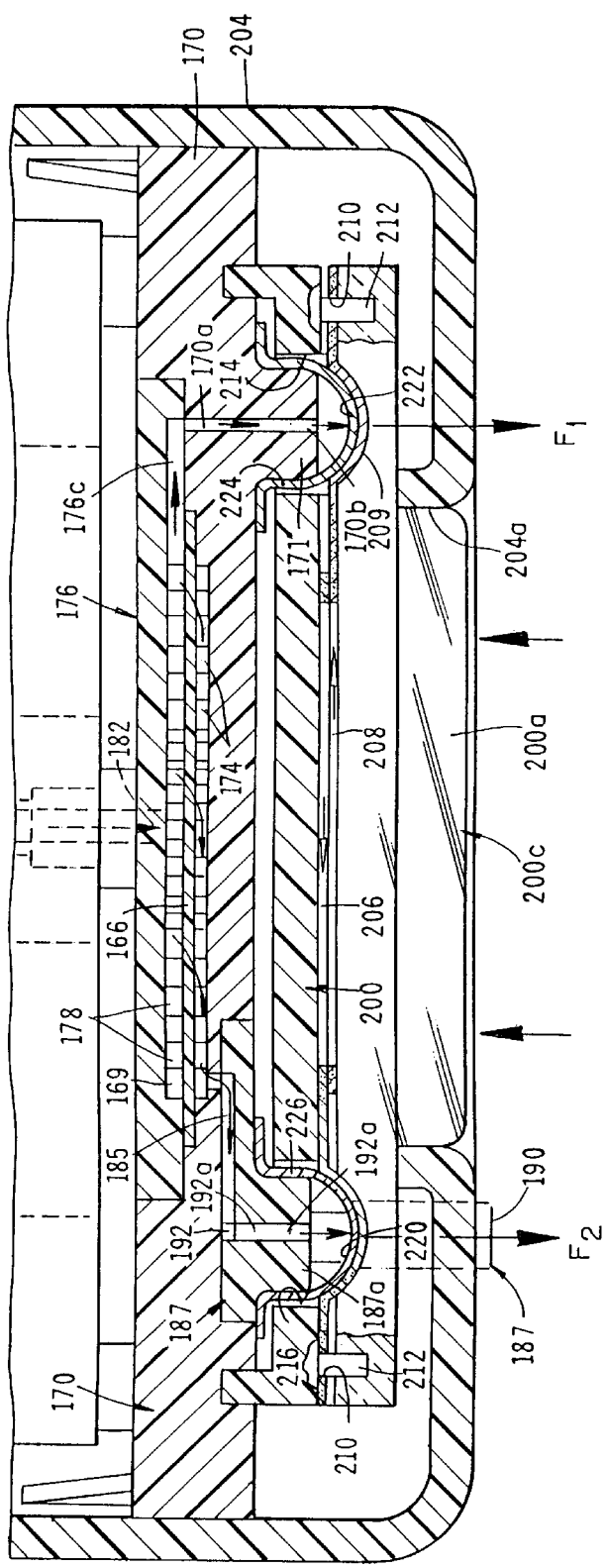
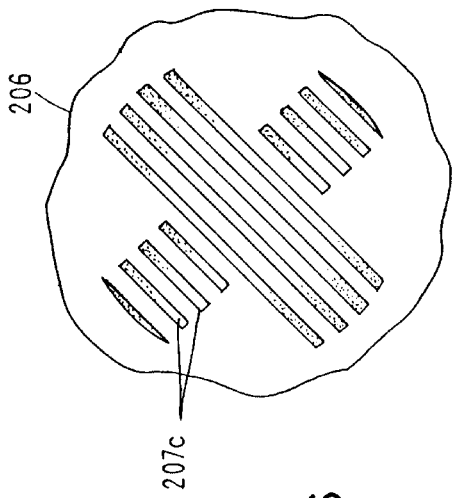
FIG. 35
FIG. 36

APPARATUS FOR INDICATING FLUID PRESSURE IN A CONDUIT

BACKGROUND OF THE INVENTION

This is a Divisional application of application, Ser. No. 08/718,686 filed Sep. 24, 1996, now U.S. Pat. No. 5,721,382 which is a Continuation-In-Part application of application, Ser. No. 08/432,220, filed May 1, 1995, now abandoned.

FIELD OF THE INVENTION

The present invention relates generally to devices for indicating fluid flow through fluid conduits. More particularly, the invention concerns a mechanical fluid flow indicator for providing a clear visual indication of fluid flow through one or more fluid conduits with which the indicator is associated.

DISCUSSION OF THE PRIOR ART

The prior art is replete with devices for detecting and measuring fluid flow through fluid conduits. The devices range from simple pressure gages to highly complex mechanical and electrical detectors and flow meters.

Fluid flow indicating devices find application in numerous fields including chemical, industrial and medical fields. In the medical field a number of diverse applications exist for fluid delivery systems that incorporate a means for indicating the status of fluid flow to the patient. For example, traditional gravity feed intravenous delivery systems often incorporate a flow indicator that is positioned in the fluid delivery line that connects the fluid reservoir of the device to the patient. As exemplified by U.S. Pat. No. 5,267,980 issued to Dirr, Jr. et al, an indicator of this type operates by passing a beam of electromagnetic energy from a light-emitting source through the drip chamber itself. The passage of a drop of fluid through the drip chamber interrupts the light beam, which, in turn is registered by a light detector situated opposite the light emitting source. In addition to optical alignment, this type of system requires an external source of energy for light emitter and assembly of the system before it can be used.

The prior art also teaches the use of electronic sensors as detectors for pole mounted pumps used for intravenous administration of drugs to a patient, usually when very accurate delivery regimens or delivery of multiple fluids are required. One such application is disclosed in U.S. Pat. No. 5,039,279, issued to Natwick et al which provides sensors to detect whether the medication is reaching the patient at the desired rate. In the Natwick et al device fail safe mechanisms work in conjunction with sensors which detect excessive flow rates and air bubbles in the line. Pole mounted pumps such as these, provide accurate systems for delivery, but are typically expensive to use and do not allow the patient to be ambulatory as they require an external power source.

A fluid flow indicator such as that described in U.S. Pat. No. 4,187,847 issued to Loeser embodies still another type of flow meter disposed in the fluid flow path of an airless fluid delivery apparatus. In this device, the flow indicator comprises a pin wheel or rotor comprised of a plurality of colored fins connected to a hub which rotates with a chamber as fluid passes through during delivery. The color pattern produced by the velocity of rotation of the rotor provides a visual indicator of the flow rate during operation of the fluid delivery system.

Yet another example of a prior art fluid flow detection system can be found in U.S. Pat. No. 4,784,648, issued to Singh et al which describes an in-line flow restrictor used in conjunction with a source of pressurized infusate. Attached to and in fluid communication with the flow restrictor on both the upstream and downstream ends are annuli, which are inflatable by infusate pressure. In operation of the Singh et al device, the upstream annulus is inflated by the delivery pressure generated by the source, while the downstream annulus inflates only when pressure builds due to infiltration of the infusion site. When inflated, the annuli provide a visual indication through a jacket constructed from frosted material or alternatively by contacting a membrane switch.

U.S. Pat. No. 3,895,631 issued to Buckles et al describes a portable, liquid infusion device which embodies still a different type of fluid flow indicator system. In the Buckles et al device, a viewing aperture and an open slot marked with a volume scale are provided on the device container cover. A visual signal appears in the viewing aperture that indicates to the patient when infusion has ceased due to a blockage present in the fluid flow path. Fluid pressure that would build up in the system should the needle or catheter become blocked causes the activation of a rotating arm that positions the signal in the view aperture on the device container. The volume scale in cooperation with an indicator arm attached to the fluid reservoir provide a means for indicating to the patient the volume of fluid remaining in the reservoir and when the reservoir is empty.

The prior art devices, while generally operating in a reasonably satisfactory manner, are often quite complex, difficult to maintain frequently require external power sources and sometimes are unreliable in long-term operation. It is these and other drawbacks of the prior art that the present invention seeks to overcome by providing a very simple, easily interpreted, and highly reliable mechanical apparatus for visually indicating fluid flow through a system or apparatus.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture to use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to one of the present inventors. Therefore, U.S. Pat. No. 5,205,820 is hereby incorporated by reference in its entirety as though fully set forth herein. Additionally, U.S. Pat. No. 5,411,480, also issued to one of the present inventors, describes various alternate constructions and modified physical embodiments of the invention. This U.S. Pat. No. 5,411,480 is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

SUMMARY OF THE INVENTION

By way of summary, the apparatus of the invention for visually indicating fluid flow through a fluid system or apparatus comprises a pair of thin, indicia bearing films disposed in an overlaying relationship. These films are shifted relative to each other by movement of mechanical actuators which are deflected solely by the pressure of the fluid within the fluid conduits of the system of the apparatus.

In the preferred form of the invention, the two films are stacked in close proximity and are constructed from a substantially transparent flexible material such as mylar. One surface of the inferior film is printed with a plurality of integrated symbols depicting various fluid flow conditions. The superior film functions as a mask over the inferior film and is printed with a pattern of diagonally extending, alternating clear and opaque stripes. The print ratio of the superior film permits viewing at any one time of only one of the symbols printed on the inferior film.

The inferior and superior films are attached at opposite ends to a support platform in a manner such that the patterned portions are in register and the nonpatterned portions cover actuator openings provided near each end of the support platform. Each film is able to move in opposing directions parallel to the film plane with its range of motion limited to one axis in the film plane. When the films move, the visible symbol pattern being viewed changes due to the transverse displacement of the printed symbols relative to the stripes on the superior film.

The mechanical actuators of the device are deflected from their initial, at-rest, generally planar position whenever there is a sufficient amount of fluid pressure present within the fluid conduit with which the particular actuator is associated. The actuator is deflected outwardly by the pressure of the fluid with sufficient force to urge the nonpatterned portion of the indicator film into an expansion space provided in a backing plate. As a portion of the film moves into the expansion space, the printed portion of the film is transversely displaced a specific predetermined distance. The displacement of the film realigns the printed symbol patterns on the inferior film with the mask pattern on the superior film causing a change in the symbols being viewable by the observer.

It is a primary object of the present invention to provide an apparatus for visually indicating the existence of fluid pressure within one or more fluid carrying conduits, which is of simple construction, is highly reliable in operation and is easily interpreted.

Another object of the invention is to provide an apparatus of the aforementioned character which in no way impedes the flow of fluid through the fluid conduits and is actuated solely by the fluid pressure of the fluid within the fluid conduits.

Another object of the invention is to provide an apparatus as described in the preceding paragraphs which distinguishes between and provides a clear indication of various conditions of fluid flow through a given fluid system or apparatus, such as normal flow, absence of fluid pressure within all or a portion of the system and abnormal or interrupted flow due to a blockage within the system.

Still another object of the invention is to provide a fluid flow indicator of the class described which is ideally suited for use in connection with medical infusion devices of the character having a fluid reservoir defined by a distendable membrane superimposed over a base, the distendable membrane being distendable by the fluid to be infused into the patient and having a tendency to return to a less distended configuration in order to urge fluid flow through a fluid conduit associated with the flow indicator.

Another object of the invention is to provide a fluid flow indicator as described in the preceding paragraphs in which normal flow of fluid from the reservoir of the infusion device is clearly indicated by indicia-carrying thin films disposed in an overlaying configuration which films are movable relative to each other by mechanical actuators operated solely by fluid under pressure flowing from the reservoir.

Yet another object of the invention is to provide an apparatus of the character described which embodies few parts, requires virtually no maintenance and can be easily and inexpensively manufactured.

Other objects of the invention are set forth in U.S. Pat. No. 5,205,820 which is incorporated herein and still further objects will become more apparent from the discussion which follows.

BRIEF DESCRIPTION OF THE DRAWINGS

FIG. 1 is a generally perspective, exploded view of one form of the fluid flow indicator apparatus of the invention.

FIG. 2 is a cross-sectional view of the apparatus of FIG. 1 as it appears in an assembled state.

FIG. 11A is a generally perspective, exploded view of the downstream portion of the apparatus of FIGS. 9 and 10 showing the flow indicator and a portion of the flow control means.

FIG. 11B is a generally perspective, exploded view of the remainder of the flow control means along with the reservoir subassembly portion of the apparatus shown in FIGS. 9 and 10.

FIG. 11C is a generally perspective, fragmentary view of a portion of the distendable membrane assembly of the apparatus.

FIG. 13 is a cross-sectional view taken along lines 13—13 of FIG. 12.

FIG. 14 is a cross-sectional view taken along lines 14—14 of FIG. 13.

FIG. 15 is a cross-sectional view taken along lines 15—15 of FIG. 13.

FIG. 16 is a view of the apparatus taken along lines 16—16 of FIG. 13.

FIG. 17 is a cross-sectional view taken along lines 17—17 of FIG. 16.

FIG. 18 is a cross-sectional view taken along lines 18—18 of FIG. 16.

FIG. 19 is a cross-sectional view taken along lines 19—19 of FIG. 16.

FIG. 20 is a generally perspective, exploded view of the forward portion of the apparatus.

FIG. 21 is a front view of the apparatus.

FIG. 21A is a cross-sectional view taken along lines 21A—21A of FIG. 21.

FIG. 25 is a generally perspective view of the output port of the apparatus.

FIG. 26 is a front view of the output port shown in FIG. 18.

FIG. 27 is a cross-sectional view taken along lines 27—27 of FIG. 26.

FIG. 28 is a bottom view of the luer valve fitting of the apparatus.

FIG. 29 is a cross-sectional view taken along lines 29—29 of FIG. 28.

FIG. 30 is an enlarged front view of the indicia carrying thin films of the apparatus of the invention.

FIG. 31 is a cross-sectional view similar to FIG. 21A showing the indicator means of the invention in its starting configuration.

FIG. 32 is a fragmentary front view showing the symbol that is viewable by the user when the apparatus is in the configuration shown in FIG. 31.

FIG. 35 is a cross-sectional view similar to FIG. 31, but showing the indicator means as it appears when there is a blockage downstream of the indicator means that prevents normal fluid flow.

FIG. 36 is a fragmentary front view showing the symbol that is viewable by the user when the apparatus is in the configuration shown in FIG. 35.

DESCRIPTION OF THE INVENTION

Figure 3:
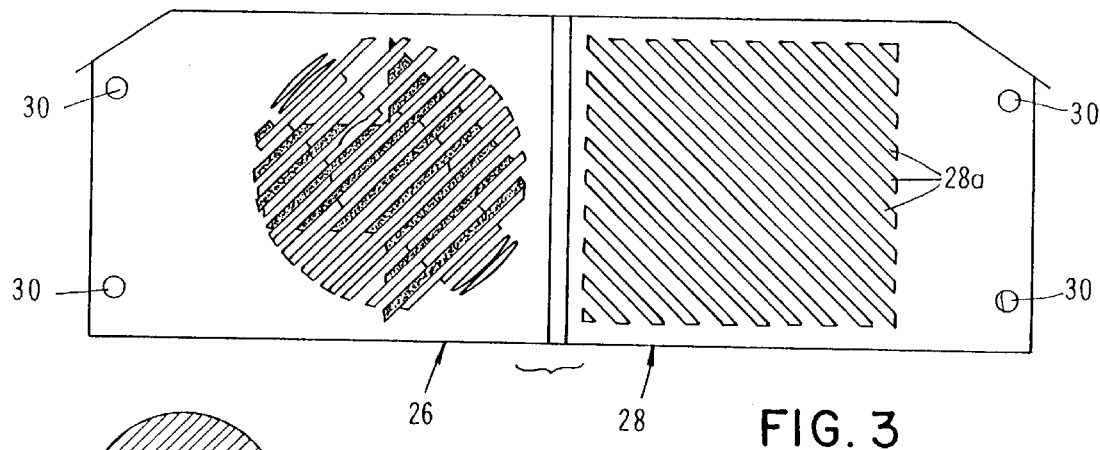
FIG. 3 is a front view of a pair of indicia bearing films of the apparatus which are adapted to be disposed in an overlaying configuration.

Referring to the drawings and particularly to FIGS. 1 and 2, one form of the fluid flow indicator means of the invention is there shown in fluid communication with a main fluid supply line 14 that branches into first and second feeder lines or conduits 16 and 18 respectively. The indicator means here comprises an indicator base or platform 20 which is connected to a support or lens plate 22 having a viewing lens portion 22a. Connected to a substrate 24 is an outlet port assembly 25 which has a fluid outlet port 25b.

Figure 6:
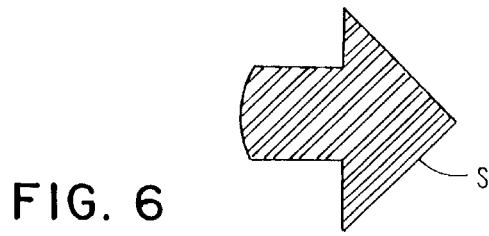
FIG. 6 is a generally diagrammatic front view showing the symbol that is viewable when the films are in the position shown in FIG. 5.
Figure 8:
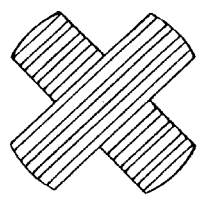
FIG. 8 is a generally diagrammatic frontview showing the symbol that is viewable when the films are in the position shown in FIG. 7.

Disposed between platform 20 and plate 22 are first and second indicia-carrying means shown here as thin films 26 and 28. Films 26 and 28, which are in intimate contact, are preferably constructed from a substantially transparent, flexible material such as mylar. It is to be understood that the indicia-carrying means can take various forms and can comprise any structure having a surface that will display a selected indicia. As indicated in FIG. 3, the downstream surface of the inferior or first film 26 is printed with three integrated symbols "S", namely, a blue circle, a green arrow, and a red X, each consisting of diagonal stripes of color printed in an alternating pattern as, for example, blue, green, red, blue, green red, and so on (see also FIGS. 4, 6, and 8). The superior, or second film 28 serves as a "mask" over the inferior film and is printed with a pattern of diagonal alternating clear and opaque stripes 28a that occur in a 1:2 ratio (FIG. 3). The printed ratio of the superior "mask" allows only one colored symbol to appear at a time when viewed through a viewing lens portion 22a provided in plate 22.

The inferior and superior films are provided at their opposite ends with apertures 30 that receive retention pins 32 provided on platform 20 (FIG. 1) which permit attachment of the film to platform 20 in a manner such that the patterned portions of the films are in index and the non-patterned portions of the films cover actuator slots 34 and 36 provided proximate each end of platform 20. With this construction, each thin film is able to move in opposing directions parallel to the film plane with its range of motion limited to one axis in the film plane by edge guides 38 provided on platform 30 (FIG. 1). As the films move, the visible symbol pattern viewed through viewing lens 22a changes due to the transverse displacement of the patterns imprinted on the films (see FIGS. 4 through 8).

Referring to FIG. 2, it is to be noted that support plate 22 is provided with transversely spaced, channel-like depressions 40 and 42 which index with slots 34 and 36 respectively when the components are assembled in the manner shown in FIG. 2. Aligned with slots 34 and 36 are mechanical actuator means here provided as yieldably deformable mechanical actuators such as thin elastomeric elements 44 and 46. More particularly, first actuator element 44 aligns with slot 34 while the second actuator element 46 aligns with slot 36.

Figure 5:
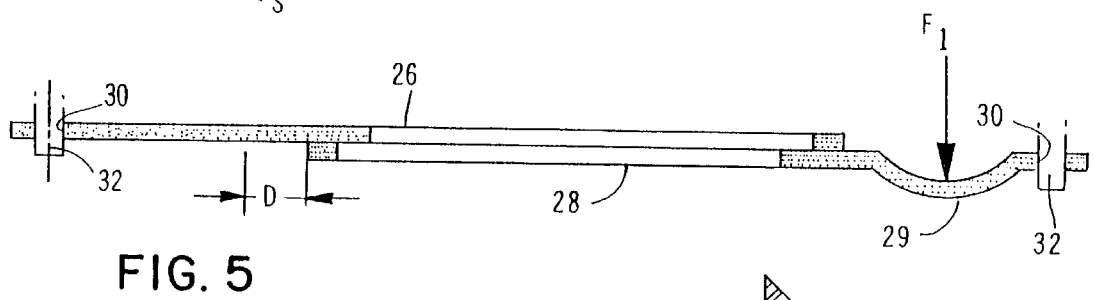
FIG. 5 is a generally diagrammatic top view showing the pair of indicia bearing films of the apparatus in a shifted position indicating fluid flow through the device.
Figure 33:
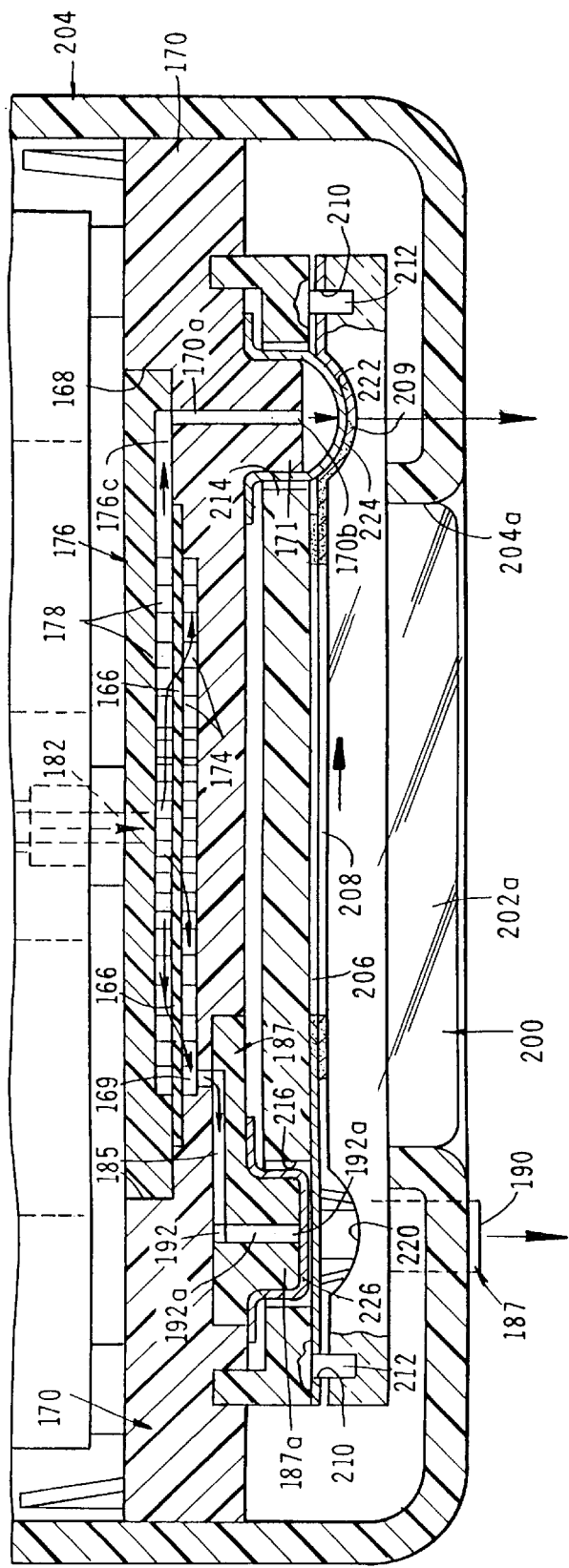
FIG. 33 is a cross-sectional view similar to FIG. 31, but showing the indicator means as it appears when fluid is flowing through the apparatus in a normal fashion.

In the manner presently to be described, the mechanical actuator elements are deflected outwardly from their initial configuration whenever there is sufficient fluid pressure present within the feeder lines to cause their outward deflection as a result of fluid under pressure impinging on the actuator means via small apertures 50 and 52 provided in substrate 24. More particularly, during operation of the apparatus the first mechanical actuator element 44 is deflected by fluid pressure F-1 of fluid flowing through first conduit 16 and through aperture 50 provided in substrate 24. As depicted in FIGS. 5 and 33, as the first mechanical actuator means is deflected outwardly by fluid force F-1, the non-patterned portion 29 of indicator film 28 will be urged into expansion channel 40. As the film arches into channel 40, the printed portion of the film is transversely displaced a specific distance "D" (FIG. 5). This film displacement re-aligns the printed symbol patterns on the inferior film 26 with the mask pattern on the superior film 28 and results in a change of the symbol (in this case the arrow shown in FIG. 6) that is visible through the support plate viewing aperture 22a.

Figure 7:
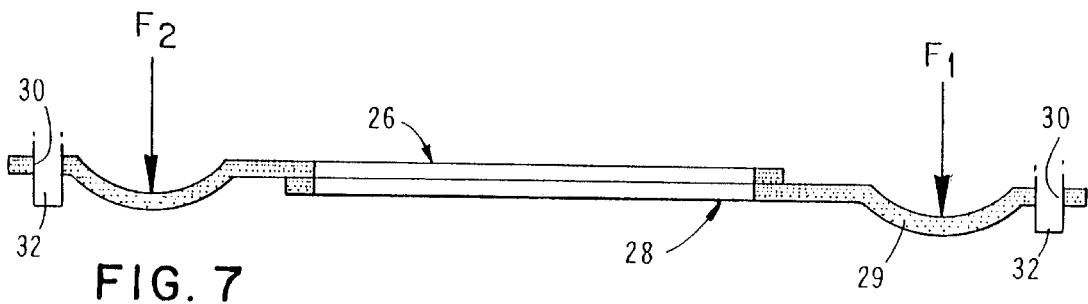
FIG. 7 is a generally diagrammatic top view showing the pair of indicia bearing films of the apparatus in shifted position indicating an absence of fluid flow through the outlet port of the device.

As can be understood by referring to FIGS. 7 and 35, both the first and second mechanical actuator elements 44 and 46 are deflected outwardly toward their respective extension channels when feeder lines 16 and 18 are pressurized by fluid forces F-1 and F-2. While first elastomeric element 44 will be deflected by line pressure F-1, second elastomeric element 46 is constructed so that a greater pressure F-2 is required to cause its deflection. In the present embodiment of the invention, this occurs when fluid is not flowing through outlet port 25b thereby causing pressure buildup within a passageway 53 leading to aperture 52 (FIG. 2). When both mechanical actuators are deflected outwardly in the manner shown in FIG. 7, both the superior and inferior films are displaced transversely to a second position revealing a second symbol, as for example, an X as viewed through the viewing aperture of the support plate (see FIGS. 8 and 36).

Figure 4:
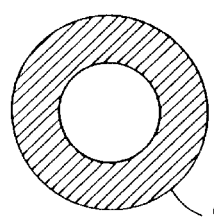
FIG. 4 is a generally diagrammatic front view showing the symbol that is viewable when the films are in their initial starting position.

A third alignment of symbol patterns as indicated in FIGS. 3, 4, 31, and 32 is visible when the device is in an unfilled state or when no fluid is flowing through conduits 16 and 18. In this instance, there is no fluid pressure exerted on either of the first and second mechanical actuator elements and, therefore, the elements remain in a non-deflected configuration. Accordingly, the inferior and superior films are not transversely displaced and thus exhibit a third combination of patterns resulting in a third symbol as, for example, a circle being visible through the viewing aperture of the support plate (FIGS. 4 and 32). The actuator elements can be specially tailored to appropriately deflect under various pressure conditions thereby making the apparatus extremely versatile.

A particularly attractive use for the apparatus of the present invention is found in the medical field. More particularly, because of the simplicity, reliability and ease of use of the indicator devices of the invention, their use in combination with medical infusion devices provides an elegant means for providing a clearly interpreted visual display of the operating condition of the infusion device. Such a use is illustrated in FIGS. 9 through 36 wherein the indicator apparatus of the invention comprises one of the three major operating subsystems of a novel ambulatory medical infusion device 130 for delivering beneficial agents, such as medicaments to a patient.

Referring particularly to FIGS. 9 through 16, the apparatus there shown comprises three major cooperating subassemblies namely, a reservoir subassembly, a flow rate control subassembly, and a flow indicator subassembly which embodies a form of indicator means somewhat similar to that shown in FIGS. 1 and 2. Each of the three subassemblies will be discussed in detail in the paragraphs which follow.

Considering first the reservoir subassembly shown in FIG. 11B, this subassembly includes a base assembly 132, a stored energy source, or distendable membrane assembly 134, and a cover 136 for enclosing the stored energy source and the base assembly (see also FIGS. 13 and 14). The base assembly includes a ullage substrate 138 and a membrane capture housing 140 having a bottom opening 142 which receives the distendable membrane engaging element or protuberance 144.

Figure 9:
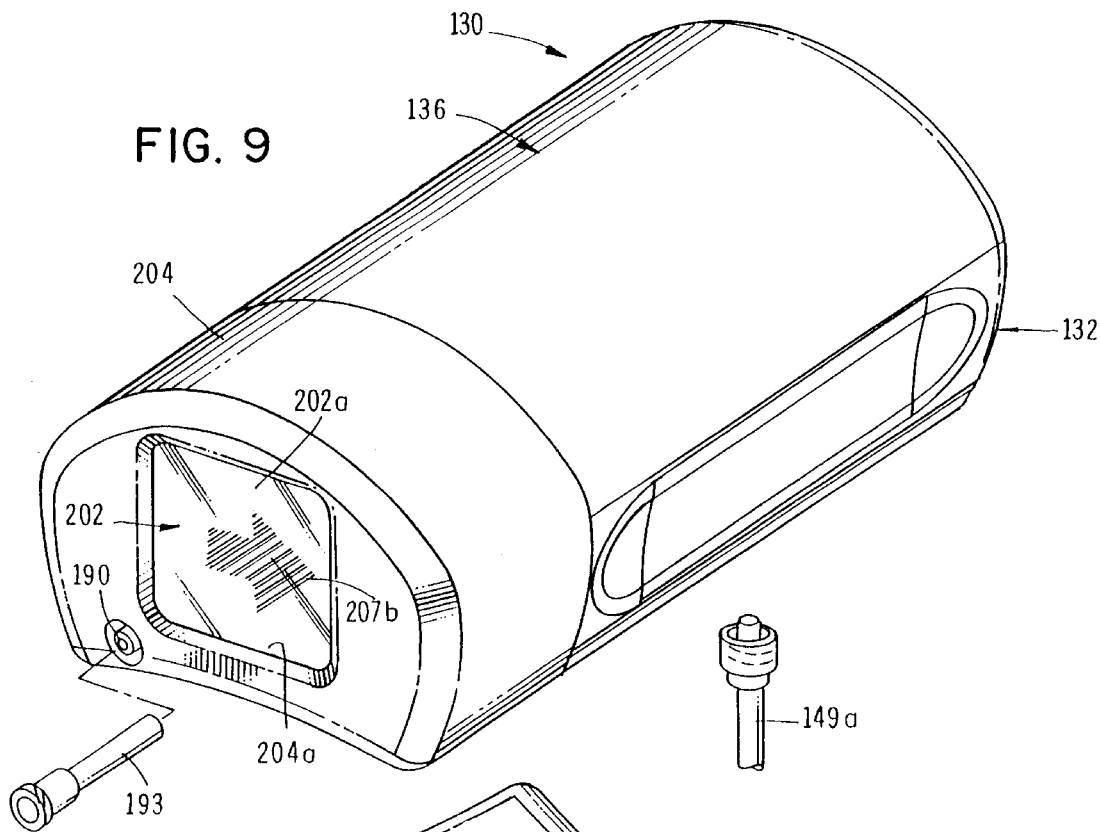
FIG. 9 is a generally perspective top view of an alternate form of the apparatus of the invention showing the flow indicator embodied in a medical infusion device of the character used to infuse medicinal fluids into a patient.
Figure 10:
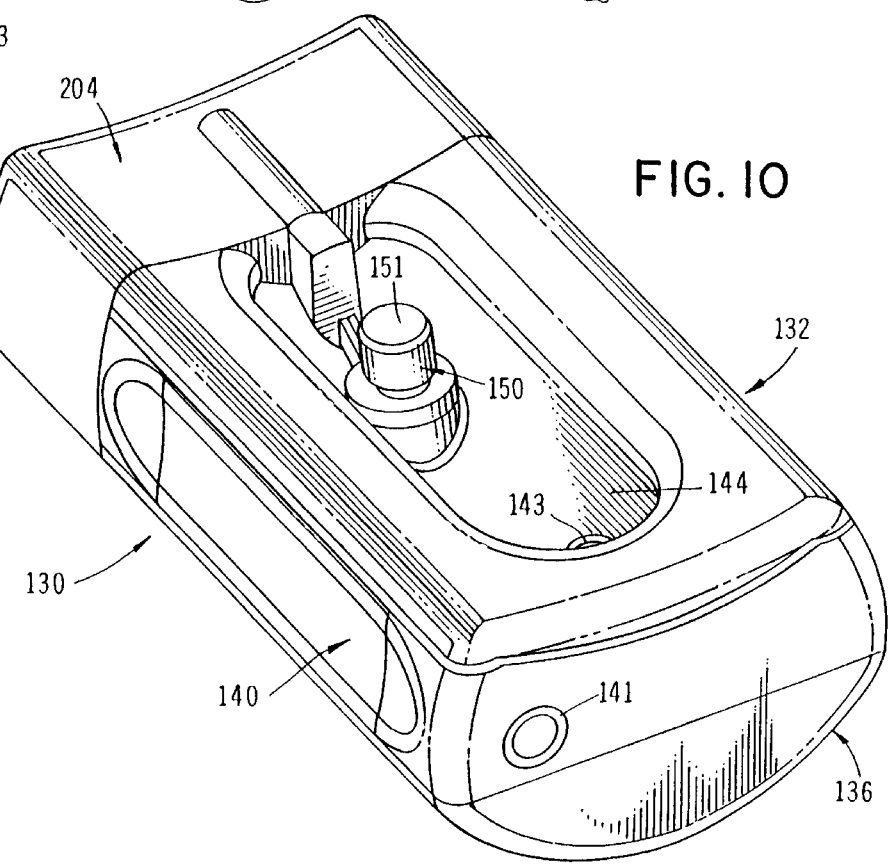
FIG. 10 is a generally perspective, bottom view of the apparatus shown in FIG. 9.
Figure 12:
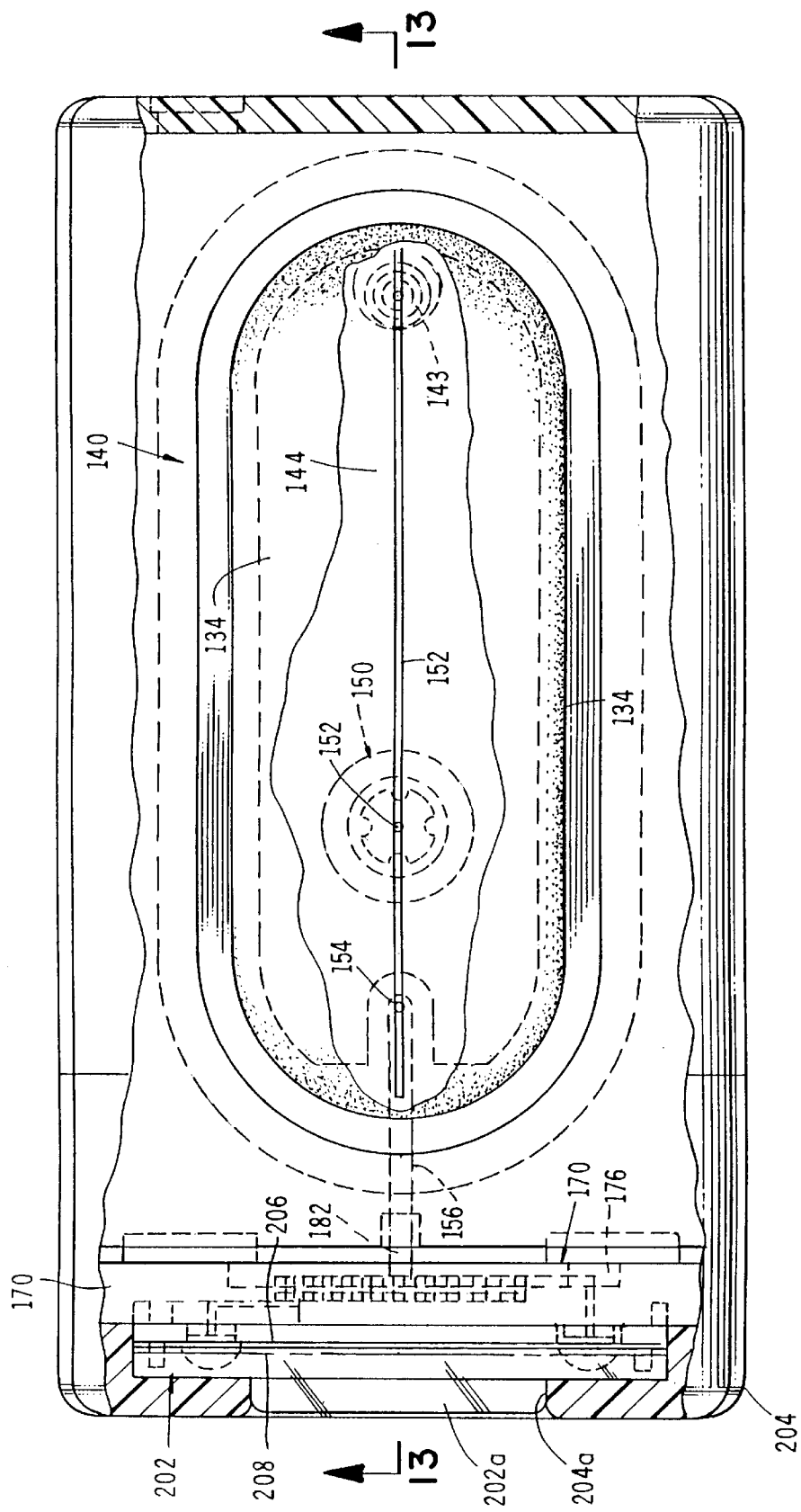
FIG. 12 is a top plan view of the apparatus, partly broken away to show internal construction.

Referring particularly to FIGS. 11B and 13, the ullage substrate 138 comprises, in addition to the distendable member engaging protuberance or ullage 144, filling means which enables the fluid reservoir 146 formed between protuberance 144 and distended membrane 134 to be filled. This filling means here includes a fluid inlet 148 provided in a luer valve fitting 150, the character of which will presently be described. Filling 150 is adapted to be interconnected with a filing conduit 149a (FIG. 9). Protuberance 144 is provided with a longitudinally extending fluid passageway 152 (FIG. 11B) which communicates with fluid passageways 154 and 156 provided in the base portion 138a of ullage substrate 138 (see also FIGS. 13 and 14).

Base portion 138a of ullage substrate 138 includes an upstanding tongue 160 which extends about the perimeter of the base portion and is closely receivable within a groove 162 formed in the base of membrane capture housing 140 (FIGS. 11B and 13). When the ullage substrate and the membrane capture housing are assembled in the manner shown in FIG. 13, the periphery of distendable membrane assembly 134 will be securely clamped within groove 162 by tongue 160. After the parts are thus assembled, housing 140 is bonded to substrate 138 by any suitable means such as adhesive or sonic bonding. This done, cover 136 is mated with housing 140 in the manner shown in FIG. 13 and bonded in place. Cover 136 is preferably constructed from a substantially transparent plastic material which is impermeable to fluids, including gases.

Filling of reservoir 146 is accomplished by introducing fluid under pressure into inlet passageway 148 and thence into reservoir 146 via filling conduit 149a and luer fitting 150. As the fluid under pressure flows into the reservoir, it will cause membrane assembly 134 to distend outwardly from protuberance 144 in the manner shown in FIG. 13. Luer fitting 150 includes a skirt portion 150a, a valve seat 150b and a biasing spring 150c which biases a ball check valve 168 toward seat 150b (see also FIG. 29). Ball 168 will lift from seat 150b against the urging of spring 150c during reservoir filling, but will sealably engage seat 150b after the reservoir has been filled. Inlet 148 is closed by a closure cap 151 prior to and following the filling step.

While the stored energy means can be in the form of a single prestressed or unstressed isotropic, elastomeric distendable membrane, it is here shown as a laminate assemblage made up of a plurality of initially generally planar distendable elements or films. Referring particularly to FIG. 11C, the stored energy means can be seen to comprise a laminate assemblage made up of individual layers 134, 134a, 134b, 134c, and 134d. Assemblage 134, which is typically prestressed, cooperates with ullage substrate 138 to define a fluid chamber, or reservoir 146. By constructing the stored energy means from a composite of distinct elements or layers, the elastic characteristics of the stored energy means can be precisely tailored to meet end application requirements. As previously discussed, as the distendable membrane assemblage 134 is distended by the fluid pressure exerted by the fluid flowing into inlet 148, internal stresses are formed therein which continuously urge the assemblage toward engagement with protuberance 144 as the assemblage tends to return toward its original configuration. As assemblage 134 moves toward protuberance 144, fluid within reservoir 146 will be uniformly and controllably forced outwardly through longitudinally extending passageway 152 in protuberance 144 and then into passageways 154 and 156 of portion 138a of ullage substrate 138. Various types of hard plastic materials that can be used to construct the base assembly and the cover. Similarly, the membrane assemblage can be constructed from a wide variety of elastomers and similar materials of a character well known in the art.

Turning next to a consideration of the flow rate control subassembly of the invention, this subassembly includes novel flow control means which are disposed externally of reservoir 146 for controlling the rate of fluid flow of fluid from the device. In the embodiment of the invention shown in FIGS. 9 through 36, the flow control means comprises a rate control membrane 66 (FIG. 11A) which is closely received within a circular recess 168 formed in support means shown here as a membrane support structure 170. The downstream wall 172 of recess 168 is provided with fluid distribution means comprising a multiplicity of circumferentially spaced, arcuate-shaped, manifolding stand-off elements 174 against which membrane 166 is held in engagement by a disc-like member 176 (FIG. 13) which is receivable within recess 168 (see also FIG. 22). As best seen by also referring to FIGS. 19 and 22, member 176 is provided with fluid collection means shown here as a multiplicity of circumferentially spaced, manifolding stand-offs 178 which engage membrane 166 when member 176 is in position within cavity 168. More particularly; as indicated in FIG. 13, when member 176 is in place within cavity 168, the flow control membrane 166 is bonded at its circumference to member 170 and is securely positioned between stand-offs 174 and 178 which cooperate to define a multiplicity of concentric and radial extending fluid passageways, which function to direct fluid flow through the flow control means. Air within chamber 168 is vented via vent patch 192a and opening 192b (FIG. 11B).

Figure 22:
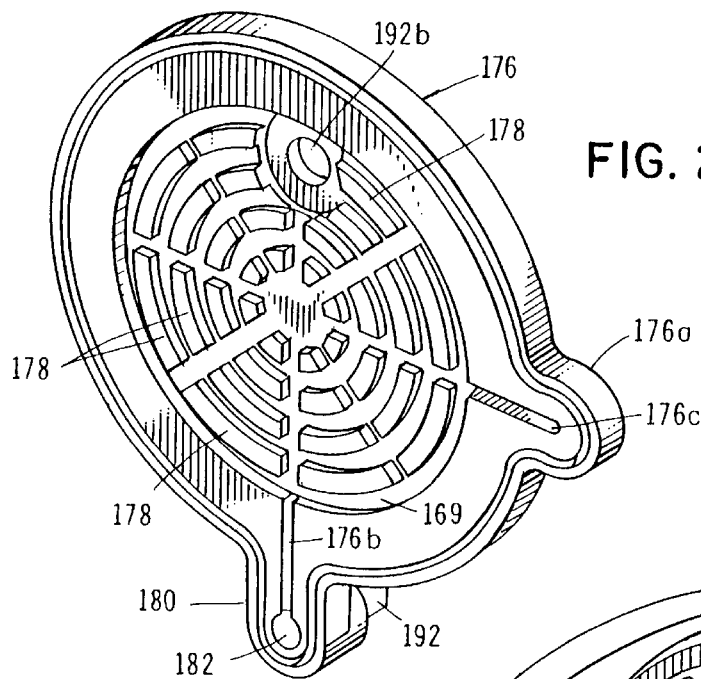
FIG. 22 is a generally perspective view of the cover for the rate control apparatus of the invention.
Figure 23:
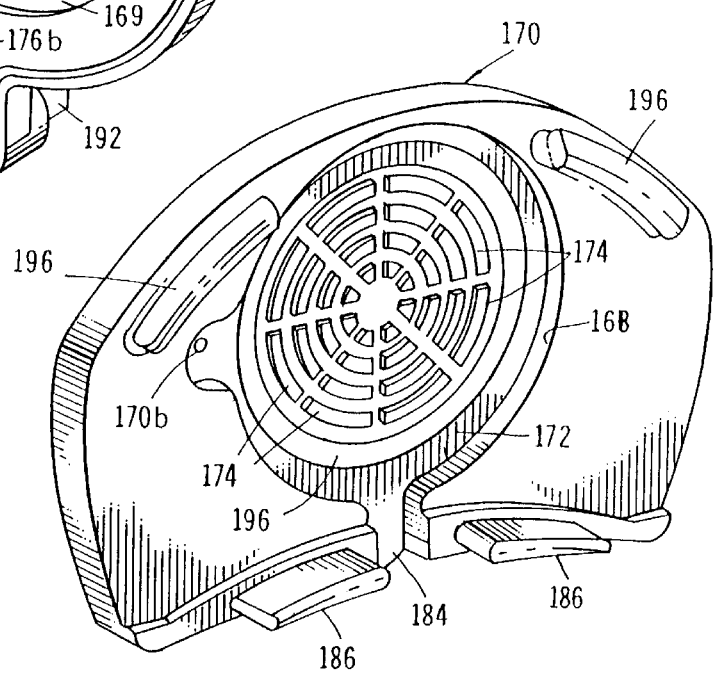
FIG. 23 is a generally perspective, front view of the substrate portion of the rate control apparatus.
Figure 24:
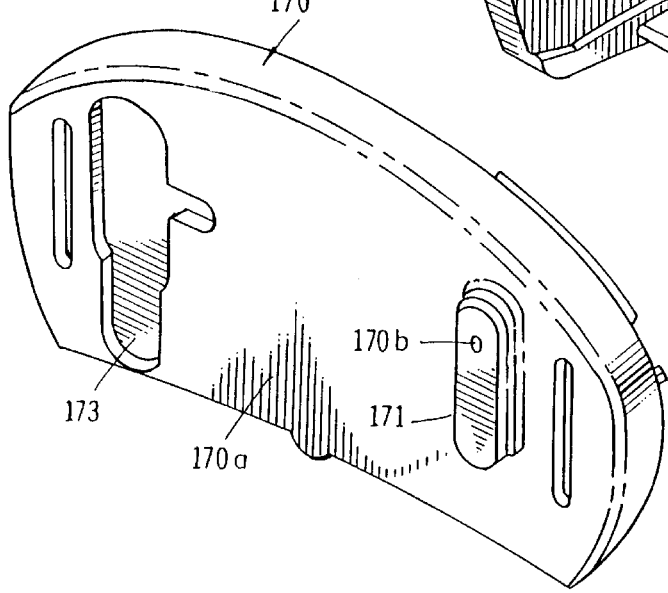
FIG. 24 is a generally perspective rear view of the substrate portion.

As best seen in FIGS. 11B and 22, member 176 includes a downwardly extending fluid inlet leg or segment 180 which is provided with a fluid passageway 182. Passageway 182 is adapted to communicate with chamber 168 when member 176 is mated with support structure 170. As shown in FIG. 23, support structure 170 has a centrally disposed recess 184 that receives inlet segment 180.

Formed on either side of recess 184 are wing-like protuberances 186 that are received within spaced-apart, arcuate-shaped cavities 188 formed in the base portion 138a of ullage substrate 138. Also formed in substrate 138 is a socket 190 (FIG. 13) which closely receives a tubular extension 192 formed as a part of inlet segment 180. Located proximate the upper edge of support structure 170 are spaced-apart capture grooves 196, which attach cover 136 to member 170.

As shown in FIGS. 13 and 17, when the flow control subassembly is mated with the reservoir assembly, fluid inlet passageway 182 of member 176 is placed in fluid communication with reservoir 146 via passageways 154 and 156. With this construction, when fluid is forced through fluid passageway 152 of protuberance 144 by the stored energy means, the fluid will flow into passageway 154, next into passageway 156 then into passage 182 of member 76, and finally into chamber 168 formed in member 170. As the fluid under pressure flows into the upstream portion of chamber 168 behind membrane 166, it will be distributed by standoffs 178 so that it will uniformly flow through membrane 166 and toward the fluid outlet port of the flow control subassembly. As best seen in FIGS. 19 and 25, the outlet port comprises an assembly 187 which is receivable in a cavity 173 formed in the back of downstream wall 170a of the substrate 170. Assembly 187 includes a fluid outlet 190 and an internal chamber 192, the purpose of which will presently be described. During filling of chamber 192, air therewithin can be vented to atmosphere via vent patch 92a.

The flow control means of this form of the invention is shown as comprising a single layer of permeable material having the desired fluid flow characteristics. However, the flow control means can also comprise an assemblage of a plurality of layers of permeable materials, P-1, P-2, and P-3 of the character seen in FIG. 31 of U.S. Pat. No. 5,205,820 issued to the present inventors. These layers, which may be composites, thin films, or porous substrates, may be constructed of any one of the materials described in U.S. Pat. No. 5,205,820 so that the fluid pressure flow characteristics of the assemblage can be precisely tailored for the particular medicinal or other fluid being dispensed. Reference should be made to U.S. Pat. No. 5,205,820 which patent is hereby incorporated herein in its entirely as though fully set forth herein, for a further description of the construction and operation of the flow control membrane and for a further discussion of the materials that can be used to construct the base, the cover and the stored energy means.

Considering now the flow indicator means of this embodiment of the invention, this novel means visually distinguishes among three conditions of operation, namely normal fluid flow, fluid flow blockage, and reservoir empty. Turning to FIG. 11A, the flow indicator means here comprises an indicator base or platform 200, a support or lens plate 202, and a hollow housing 204 within which the platform and the support plate are mounted. As seen in FIG. 21, plate 102 has a viewing lens 202a which indexes with an aperture 204a provided in housing 204.

Disposed between platform 200 and plate 202 are first and second indicia-carrying means shown here as thin films. These films, identified here as 206 and 208, are in intimate contact and are constructed from a substantially transparent, flexible material such as mylar. Once again, the indicia-carrying means can be any surface presenting member upon which indicia can be provided. The downstream surface of the inferior or first film 206 is printed with three integrated symbols 207 (FIG. 30), namely, a blue circle 207a (FIG. 32), a green arrow 207b (FIG. 34), and a red X 207c (FIG. 36), each consisting of diagonal stripes of color printed in an alternating pattern (blue, green, red, blue, green red, and so on (FIGS. 30 through 36)). The superior, or second film 208 serves as a "mask" over the inferior film 206 and is printed with a pattern of diagonal alternating clear and opaque strips 108a that occur in a 1:2 ratio. The printed ratio of the superior "mask" allows only one colored symbol to appear at a time when viewed through viewing lens 202a in plate 202. The inferior and superior films are provided at their opposite ends with apertures 210 which receive retention pins 212 provided on platform 200 (FIG. 19) which permit attachment of the film to platform 212 in a manner such that the non-patterned portions of each film covers actuator slots 214 and 216 provided proximate each end of platform 200 with the patterned portions of both the superior and inferior films being maintained in index. With this construction, each thin film is able to move in opposing directions parallel to the film plane with its range of motion limited to one axis in the film plane by edge guides 218 provided on platform 200 (FIG. 19). As the films move, the visible symbol pattern changes due to the transverse displacement of the patterns imprinted thereon.

Referring particularly to FIGS. 11A and 17, it can be seen that support plate 202 is provided with transversely spaced, channel-like depressions 220 and 222 which index with slots 214 and 216 respectively when the components are assembled in the manner shown in FIGS. 17 and 21. Aligned with the upstream (reservoir) side of slots 214 and 216 are mechanical actuator means here provided as mechanical actuators or elastomeric elements 224 and 226. More particularly the first actuator element 224 covers slot 214 and the second actuator element 226 covers slot 214.

In a manner presently to be described, the mechanical actuator means are deflected from their initial configuration whenever there is sufficient fluid pressure present within the fluid flow path to cause their outward deflection toward films 206 and 208. During operation the first mechanical actuator element 224 is deflected by fluid pressure of reservoir 146. More particularly, when there is sufficient fluid pressure in the fluid reservoir and fluid is being delivered by the stored energy means of the device, the first mechanical actuator means is deflected outwardly so as to urge the non-patterned portion 209 of indicator film 208 into expansion channel 222. As the film arches into channel 222, the printed portion of the film is transversely displaced a specific distance. This film displacement re-aligns the printed symbol patterns on the inferior film 206 with the mask pattern on the superior film 208 and results in a change of the symbol (in this case an arrow) see FIGS. 33 and 34 that is visible through the support plate viewing lens 202a.

Figure 34:
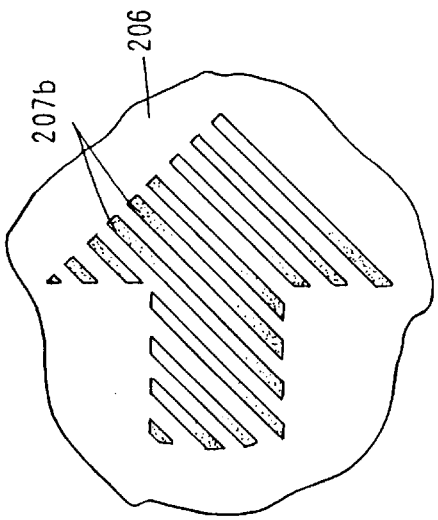
FIG. 34 is a fragmentary front view showing the symbol that is viewable by the user when the apparatus is in the configuration shown in FIG. 33.

As can be observed by referring to FIG. 34, both the first and second mechanical actuator elements 224 and 226 are deflected outwardly toward their respective extension channels when the device is filled and primed but not in a state of delivery or when there is a build up of fluid pressure during delivery that is caused by blockage of the delivery line downstream from second mechanical actuator element 226. While element 224 can be deflected by normal line pressure element 226 is deflected only by pressure caused by a downstream blockage. When both mechanical actuators are deflected outwardly, both the superior and inferior films are displaced transversely to a second position revealing a second symbol, as for example, an X as viewed through the viewing aperture of the support plate (see FIG. 36).

A third alignment of symbol patterns as shown in FIG. 32 is visible when the device is in an unfilled state or when the delivery line is open, the reservoir is empty and fluid delivery to the patient has been completed. In this case, there is no fluid pressure in the line on either the upstream or downstream side of the flow control means and thus both the first and second mechanical actuator elements are in a non-deflected position. In this condition, the inferior and superior films are not transversely displaced and thus exhibit a third combination of patterns resulting in a third symbol as, for example, a circle being visible through the viewing aperture of the support plate (see FIGS. 31 and 32).

In considering the method of operation of the device and the manner in which fluid flow through the device, reference should be made particularly to FIGS. 13, and 31 through 36. During the filling step, the fluid to be dispensed is introduced into reservoir 146 via a fluid inlet conduit 149a (FIG. 9) which is connected to luer fitting 150. Fluid flowing into the fitting lifts check valve ball 168 against the urging of spring and causes the distendable membrane assembly to be displaced away from ullage protuberance 144 in the manner shown in FIG. 13. Air within housing 140 and cover 136 will be suitably vented to atmosphere via a vent 141 which is receivable within a vent aperture 141a provided in housing 140 (FIG. 11B). During the filling step, the gaseous component of the fluid is vented to atmosphere via a vent patch 143 provided in portion 138a of substrate 138 (FIGS. 11B and 13).

During the fluid dispensing step, the prestressed membrane assembly will tend to return toward a less distended configuration causing fluid within the chamber to flow outwardly of passageway 152 and into passageways 154 and 156. The fluid under pressure will next flow into passageway 182 of disc-shaped member 176. Turning particularly to FIGS. 17 and 22, it is to be observed that a portion of the fluid entering chamber 168 of member 170 from passageway 182 and upstream of membrane 166, can flow directly toward an ear-shaped extension 176a provided on member 176 via flow passageways 176b and 176c. From passageway 176c, the fluid will flow under pressure into passageway 170a formed in substrate 170 and toward passageway outlet 170b. Fluid flowing through outlet 170b will impinge directly upon flow indicator element 224 which sealably engages a protuberance 171 formed on substrate 170 causing element 224 to deform outwardly in a manner to force portion 209 of indicator film 208 to arch into expansion channel 222. This, in turn, will cause transverse displacement of indicator film 208 in the manner previously described.

Fluid flowing through passageway 182 of disc-shaped member 176 will also be distributed over the upstream face of the rate control membrane 166 by the fluid distribution means, or protuberances 178 and will pass through the membrane at a predetermined controlled rate. The fluid flowing through the rate control membrane will be collected by the fluid collection means or protuberance 174 and then will flow via passageway 185 into passageway 192 of outlet port assembly 187. The fluid will then flow outwardly of the device through fluid outlet 190 to which an infusion line 193 is connected (FIGS. 9, and 33). It is to be observed that a portion of the fluid flowing into outlet port assembly 187 is free to flow through passageway 192a provided in a protruding portion 187a thereof. If there is a blockage which prevents free fluid flow outwardly of the device through outlet 190 and infusion line 193, fluid buildup pressure F-2 caused by the blockage will act upon indicator element 226 causing it to deflect outwardly. This outward deflection of element 226 will urge a portion of indicator film 206 into receiving channel 226 of the lens plate causing transverse movement of film 206 so as to reposition film 206 relative to film 208. Should fluid flow into chamber 192 cease, indicator element 226 will return to its at-rest position as will film 206. Similarly, if fluid flow from the reservoir ceases, film 208 will also return to its at rest position thereby once again causing the "O" symbol to be viewable through viewing lens 202a.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for use in infusing medicinal fluid into a patient at a controlled rate comprising:
   (a) a base;
   (b) stored energy means for forming, in conjunction with said base a fluid reservoir having an outlet, said energy storage means comprising at least one generally planar, distendable member having a peripheral portion affixed to said base, said member being distendable as a result of pressure imparted by the fluids to be infused, to establish internal stresses, said stresses tending to move said member toward a less distended configuration;
   (c) an outlet port in communication with said outlet of said fluid reservoir for dispensing fluids from the device; and
   (d) fluid actuated indicator means disposed intermediate said fluid outlet of said reservoir and said outlet port for visually indicating fluid flow from said fluid reservoir.

2. A device as defined in claim 1 further including flow control means disposed intermediate said indicator means and said outlet of said fluid reservoir for controlling the rate of flow of fluid from the device.

3. A device as defined in claim 1 in which said indicator means comprises first and second at least partially overlaying thin films, said films being movable relative to each other in response to fluid flowing from said fluid reservoir.

4. A device as defined in claim 3 in which said indicator means includes actuator means movable by fluid flowing from said reservoir between a first position wherein said actuator means are spaced from said thin films to a second position wherein said actuator means engage at least one of said thin films.

5. A device as defined in claim 4 in which said actuator means comprise first and second actuator elements disposed proximate said first and second thin films, said first actuator element being movable into engagement with said first film and said second actuator element being movable into engagement with said second film.

6. A device as defined in claim 5 further including flow control means disposed between said fluid outlet of said reservoir and said first and second actuator elements for controlling fluid flow through said outlet port.

7. A device as defined in claim 6 in which said flow control means comprises a permeable membrane.

8. A device as defined in claim 7 in which one of said first and second actuator elements is movable by fluid flowing from said reservoir through said permeable membrane and the other of said first and second actuator elements is movable by fluid flowing from said fluid reservoir and by passing said permeable membrane.

9. A device as defined in claim 7 in which said first and second thin films are substantially transparent and in which at least one of said first and second thin films carries indicia.

10. A device for use in infusing medicinal fluid into a patient at a controlled rate comprising:
    (a) a base;
    (b) stored energy means for forming, in conjunction with said base a fluid reservoir having an outlet, said stored energy means comprising at least one distendable member superimposed over said base, said member being distendable as a result of pressure imparted by the fluids to be infused to establish internal stresses, said stresses tending to move said member toward a less distended configuration;
    (c) an outlet port in communication with said outlet of said reservoir for dispensing fluids from the device; and
    (d) flow control means disposed intermediate said outlet of said reservoir and said outlet port for controlling the rate of flow of fluid from the device, said flow control means comprising:
       (i) a permeable membrane; and
       (ii) support means for supporting said permeable membrane within the path of fluid flowing from said outlet of said reservoir toward said outlet port.

11. A device as defined in claim 10 in which said support means of said flow control means includes fluid distribution means for distributing fluid flowing from said outlet of said reservoir toward said permeable membrane.

12. A device as defined in claim 10 in which said support means of said flow control means includes fluid collection means for collecting fluid flowing through said permeable membrane and directing said fluid toward said outlet port.

13. A device as defined in claim 10 further including fluid actuated indicator means disposed intermediate said flow control means and said outlet port for visually indicating fluid flow from said reservoir.

14. A device as defined in claim 13 in which said indicator means comprises first and second at least partially overlaying indicia-carrying thin films, said films being movable relative to each other in response to fluid flowing from said fluid reservoir, whereby selected portions of said indicia becomes visible.

15. A device for use in infusing medicinal fluid into a patient at a controlled rate comprising:
    (a) a base;
    (b) stored energy means for forming, in conjunction with said base a fluid reservoir having a fluid inlet and a outlet, said stored energy means comprising a distendable member superimposed over said base, said member being distendable to establish internal stresses, said stresses tending to return said member to less distended configuration to urge fluid flow through said fluid outlet;
    (c) an outlet port in communication with said outlet of said reservoir for dispensing fluids from the device; and
    (d) fluid actuated indicator means disposed intermediate said fluid outlet of said reservoir and said outlet port for visually indicating fluid flow from said fluid reservoir, said indicator means comprising:
       (i) a pair of thin films disposed in an overlaying relationship, at least one of said thin films having indicating indicia viewable upon relative movement of said films; and
       (ii) actuator means communicating with said fluid outlet for moving at least one of said thin films relative to the other in response to fluid pressure being exerted on said actuator means.

16. A device as defined in claim 15, further including flow control means disposed intermediate said indicator means and said outlet port for controlling the rate of flow of fluid from the device, said flow control means comprising a permeable membrane.

17. An apparatus as defined in claim 15 in which each of said pair of thin films of said indicator means has a fixedly located edge portion and body portion, at least one of said films being yieldably deformable by said actuating means to cause relative movement between said body portions of said thin films upon fluid pressure being exerted on said actuating means by fluid flowing from said reservoir whereby said indicating indicia becomes viewable.

18. An apparatus as defined in claim 17 further including a platform to which said edge portions of said pair of thin films are affixed, said platform having a central planar portion for supporting said thin films in a substantially planar overlaying configuration wherein said body portions thereof are in close proximity.

19. An apparatus as defined in claim 18 in which said platform includes an aperture and in which said actuator means comprises a yieldably deformable actuator element overlaying said aperture and disposed proximate said outlet port.

20. An apparatus as defined in claim 18 further including a support plate disposed proximate said platform for supporting said pair of thin films, said support plate having a depression aligned with said aperture in said platform, said deformable member being adapted to urge a portion of one of said thin films into said depression upon fluid pressure being exerted on said yieldably deformable element of said actuating means, whereby said body portion of said one of said thin films will be caused to move relative to said body portion of said other of said thin films.

21. An apparatus as defined in claim 20 in which said support plate includes a viewing aperture disposed in alignment with said body portions of said pair of thin films.

22. A device for use in infusing medicinal fluid into a patient at a controlled rate comprising:
(a) a base;
(b) stored energy means for forming, in conjunction with said base, a fluid reservoir having an inlet and an outlet, said stored energy means comprising a distendable member comprising a plurality of prestressed, elastic members superimposed over said base said member being distendable to establish internal stresses tending to return said member toward a less distended configuration;
(c) an outlet port in communication with said outlet of said fluid reservoir for dispensing fluids from the device;
(d) a first fluid conduit in communication with said outlet of said reservoir;
(e) flow control means disposed intermediate said outlet of said reservoir and said outlet port for controlling the flow of fluid from the device, said flow control means including a second fluid conduit in communication with said reservoir; and
(f) fluid actuated indicator means disposed intermediate said outlet of said reservoir and said outlet port for visually indicating fluid flow from said outlet of said reservoir, said fluid actuated indicator means comprising:
(i) first and second thin films disposed in an overlaying relationship, at least one of said first and second thin films having indicating indicia viewable upon relative movement between portions of said first and second films; and
(ii) actuator means communicating with said fluid outlets of said first and second fluid conduits for moving portions of said first and second films relative to each other in response to fluid pressure being exerted on said actuator means by fluid within said first and second fluid conduits.

23. An apparatus as defined in claim 22 in which each of said first and second thin films has a fixedly located edge portion and a body portion, said first and second thin films being yieldably deformable by said actuating means to cause relative movement between said body portions thereof upon fluid pressure being exerted on said actuating means by fluid within said first and second fluid conduits whereby said indicating indicia becomes viewable.

24. An apparatus as defined in claim 23 further including:
(a) a platform to which said edge portions of said first and second films are affixed said platform having spaced apart first and second apertures; and
(b) a support plate disposed proximate said platform, said first and second films being disposed between said support plate and said platform, said support plate having spaced apart first and second depressions aligned with said apertures in said platform and a viewing aperture disposed intermediate said depressions.

25. An apparatus as defined in claim 24 in which said actuator means comprises:
(a) a first actuator element aligned with said first aperture in said platform for moving a portion of said first film into said first depression in response to fluid pressure being exerted on said first actuator; and
(b) a second actuator element aligned with said second aperture in said platform for moving a portion of said second film into said second depression in response to fluid pressure being exerted on said second actuator element by fluid within said second fluid conduit.

26. An aperture as defined in claim 25 in which said first and second actuator elements comprise yieldably deformable, elements aligned with said first and second apertures of said platform.

27. A device for use in infusing medicinal fluid into a patient at a controlled rate comprising:
(a) a base;
(b) stored energy means for forming, in conjunction with said base, a fluid reservoir having a fluid inlet and a fluid outlet, said stored energy means comprising at least one distendable member superimposed over said base, said member being distendable, as a result of fluids being introduced through said fluid inlet to establish internal stresses, said stresses tending to return said member toward a less distended configuration;
(c) an outlet port in communication with said outlet of said fluid reservoir for dispensing fluids from the device;
(d) a first fluid conduit in communication with said outlet of said reservoir;
(e) flow control means disposed intermediate said fluid outlet of said reservoir and said outlet port for controlling the rate of flow of fluid from the device, said flow control means including a second fluid conduit in communication with said outlet of said reservoir; and
(f) indicator means disposed intermediate said flow control means and said outlet port for visually indicating fluid flow from said fluid reservoir, said indicator means comprising:
(i) a pair of thin films disposed in an overlaying relationship, at least one of said thin films having indicating indicia viewable upon relative movement between said films; and
(ii) actuator means communicating with said fluid outlet for moving at least one of said thin films relative to each other in response to fluid pressure being exerted on said actuator means.

28. An apparatus as defined in claim 27 in which each of said pair of thin films has a fixedly located edge portion and a body portion, at least one of said films being yieldably deformable by said actuating means to cause relative movement between said body portions of said thin films upon fluid pressure being exerted on said actuating means whereby said indicating indicia becomes viewable.

29. An apparatus as defined in claim 28, further including a platform to which said edge portions of said pair of thin films are affixed, said platform having a central planar portion for supporting said thin films in a substantially planar overlaying configuration wherein said body portions thereof are in contact.

30. An apparatus as defined in claim 29 in which said platform includes an aperture and in which said actuator means comprises a yieldably deformable actuating element overlaying said aperture and disposed proximate said outlet of said first conduit.

31. An apparatus as defined in claim 29 in which said flow control means comprises a laminate construction including at least one flow rate control membrane for controlling rate of fluid flow.

32. An apparatus as defined in claim 29 in which said flow control means comprises a laminate construction including at least one filtering membrane for filtering the fluid flowing through the flow control means.

33. An apparatus as defined in claim 29 in which said flow control means comprises a laminate construction including at least one fluid distribution membrane for distribution of fluid flowing through said membrane.

34. An apparatus as defined in claim 28 further including a support plate disposed proximate said platform for supporting said pair of thin films, said support plate having a depression aligned with said aperture in said platform, said yieldably deformable actuating element of said actuating means being adapted to urge a portion of one of said thin films into said depression upon fluid pressure being exerted on said yieldably deformable actuating element of said actuating means, whereby said body portion of said one of said thin films will be caused to move relative to said body portion of said other of said thin films.

* * * * *